United States Patent [19]

Guichet

[11] 4,024,640
[45] May 24, 1977

[54] DENTAL ARTICULATOR

[76] Inventor: Niles F. Guichet, 320 Olympic Place, Anaheim, Calif. 92806

[22] Filed: Feb. 27, 1976

[21] Appl. No.: 661,935

[52] U.S. Cl. ................................................. 32/32
[51] Int. Cl.$^2$ ..................................... A61C 11/00
[58] Field of Search ........................................ 32/32

[56] References Cited
UNITED STATES PATENTS

| | | | |
|---|---|---|---|
| 3,905,112 | 9/1975 | Swanson | 32/32 |
| 3,908,271 | 9/1975 | Derda | 32/32 |

*Primary Examiner*—Robert Peshock
*Attorney, Agent, or Firm*—Fulwider, Patton, Rieber, Lee & Utecht

[57] ABSTRACT

There is disclosed a dental articulator of the Arcon type having a centric lock mechanism including a pin carried on the upper frame member and a cooperative hook arm which is pivotally mounted on the lower frame member and movable between pin engaging and detenting and pin releasing positions. The latch mechanism is spring biased to restrain the hook arm in the pin detenting position from which it can be released by pressure application to overcome the resilient bias of a compression spring loading on the mechanism. The latch mechanism is operative to lock the upper and lower frame members together when the frame members are in their closed or centric position and when the frame members are open, freely permitting rotational movement of the members between the open and closed positions while, nevertheless, retaining the frames interlocked. The articulator is also disclosed with a simple fossa guide structure allowing for a limited degree of freedom of movement without any adjustment capability and, in an alternative embodiment, with fossa guides permitting the independent adjustability of the angle of the eninentia, immediate and progressive side shifts and, optionally with an entirely adjustable fossa including adjustable top and/or rear fossa guides.

20 Claims, 10 Drawing Figures

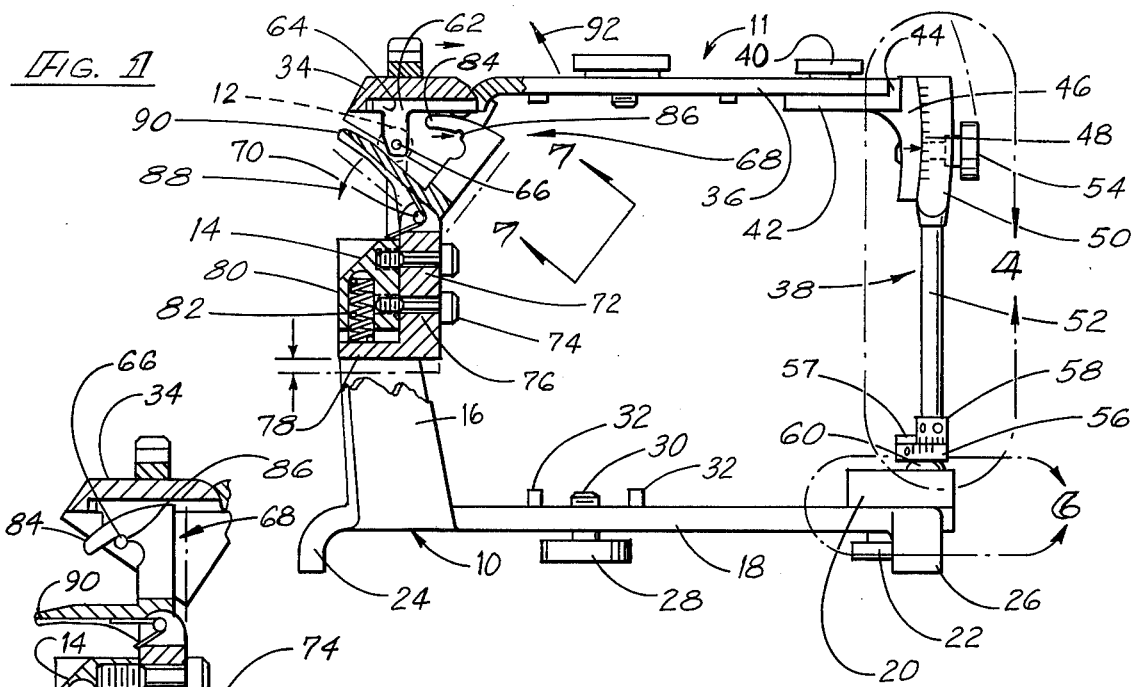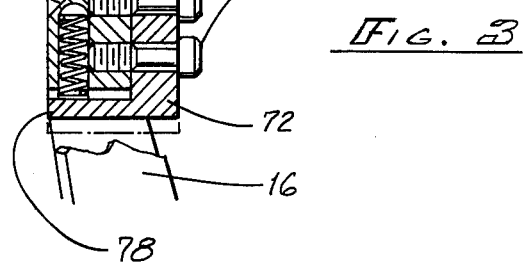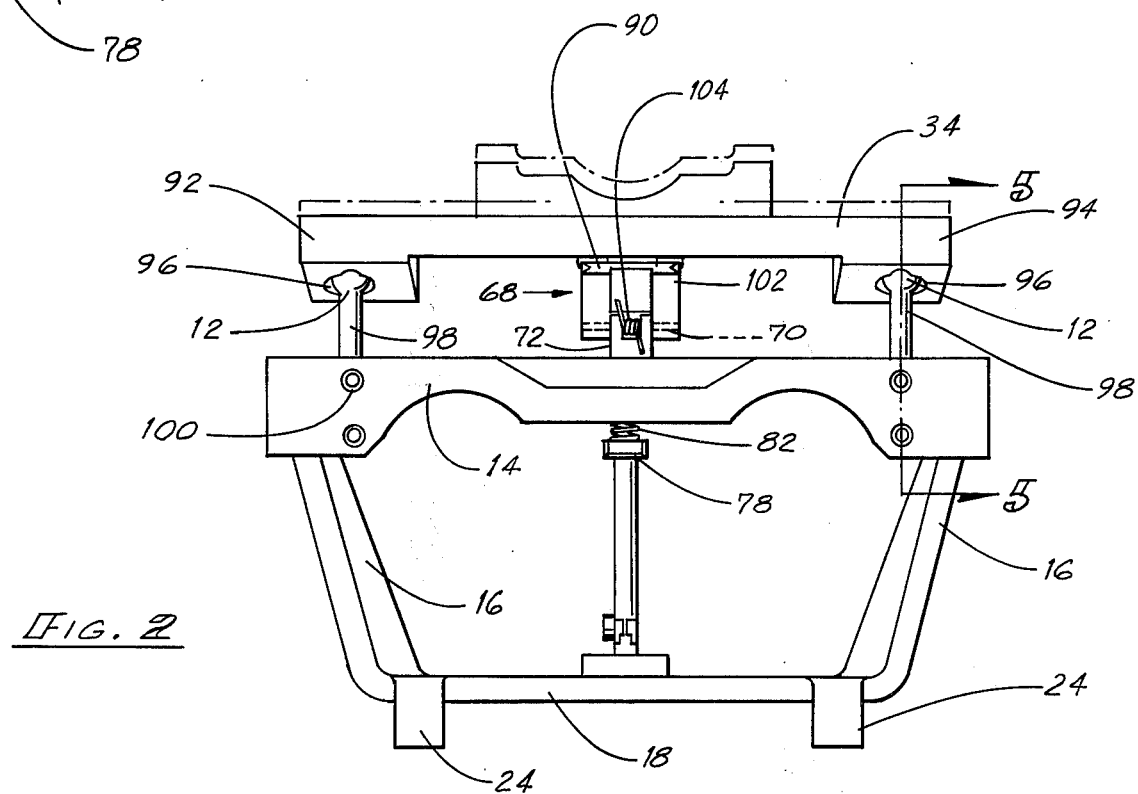

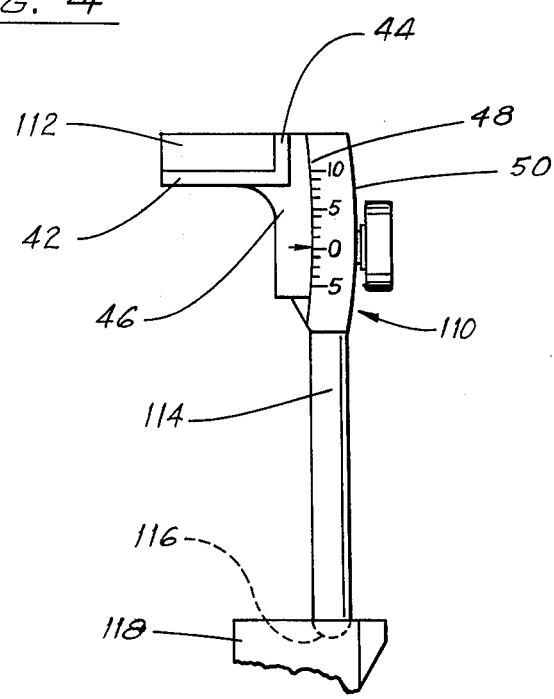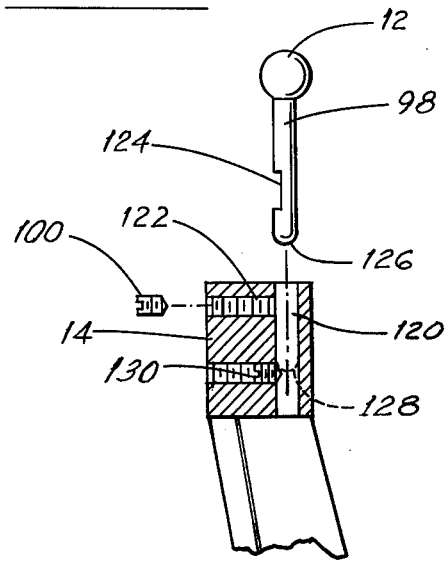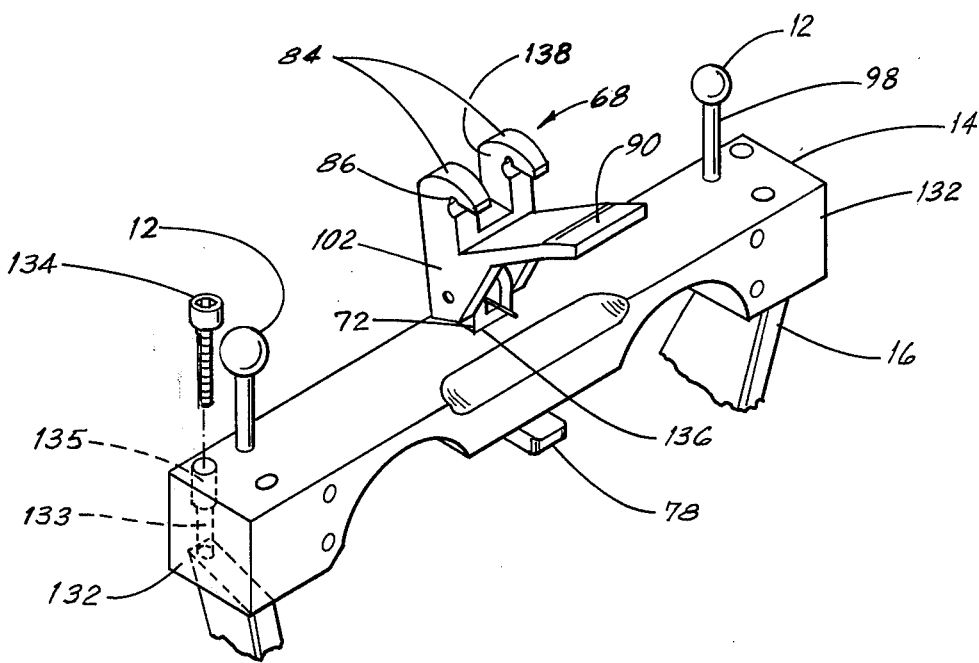

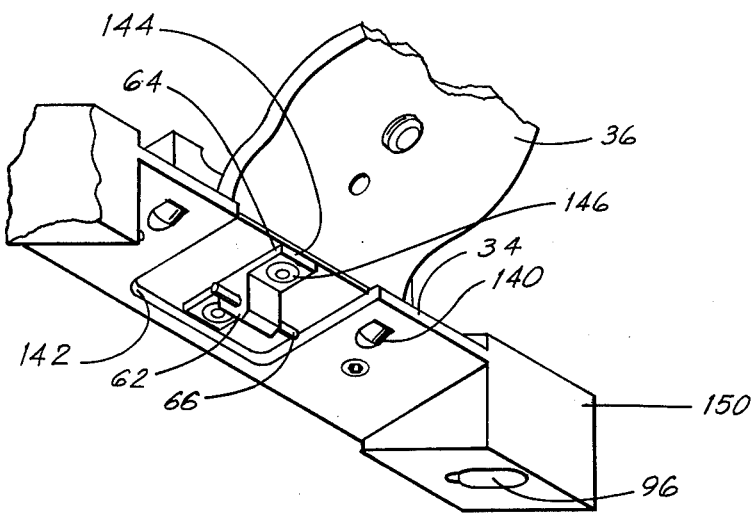
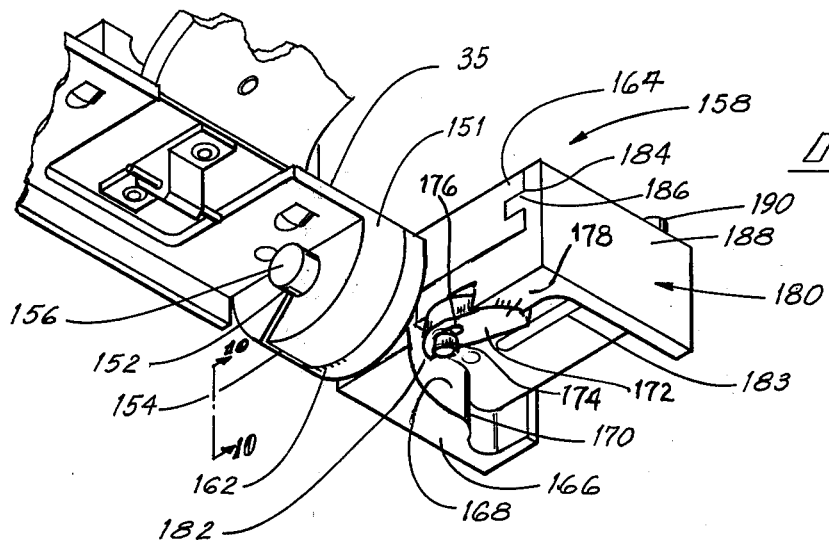
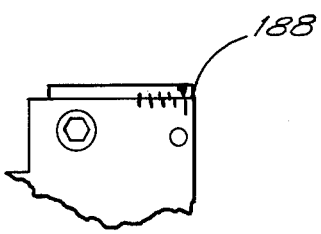
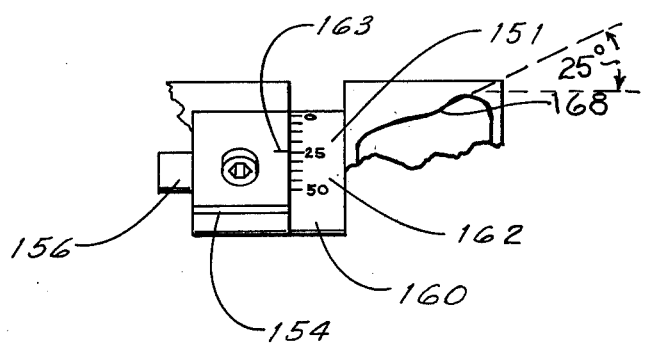

DENTAL ARTICULATOR

BACKGROUND OF THE INVENTION

1. Field of the Invention

This invention relates to a dental instrument and, in particular, to a dental articulator useful for simulating and illustrating mendibular movement.

2. Brief Statement of the Prior Art

Advances in the design and construction of dental articulators have generally been directed towards greater and greater complexity of these instruments to achieve a closer simulation and long sought duplication of mendibular movements. Some recent attempts are illustrated in U.S. Pat. Nos. 3,478,431 and 3,769,708.

The increasing complexity of these instruments increases the cost as well as the delicacy of the instruments and precludes their use for many routine clinical applications where a semi-adjustable instrument, i.e., an instrument having a limited adjustment capability is desired.

The recent generation of dental articulator development has generally followed the Arcon type instrument in which the upper frame of the articulator carries a generally box-like fossa guide assembly of superior and, optionally, posterior and media wall guide elements which cooperate with respective ones of a pair of spaced-apart spherical condylar elements carried on the lower frame member. A common shortcoming of the designs of the prior Arcon articulators has been the absence of an effective, releasable latch mechanism to interlock the upper and lower frame members. Ideally, such a latch mechanism should be operative to interlock the frame members in both the closed and opened positions yet be releasable to permit separation of the frame members. Additionally, when the instrument is provided with medial wall adjustment capability providing for an immediate side shift, i.e., entirely lateral translation of the frame members, the latch mechansim should also serve to align the frame members in a centric position. Prior designs of interlock means for Arcon type instruments are shown in the magnetic interlock of U.S. Pat. No. 2,816,366 and the centric orienting mechanism shown in the aforementioned patent.

A recent design was marketed by Schazi Company under the name Occlusomatic which featured a mechanical lock between the upper and lower frame members. This design did not permit full opening of the frame members and its marketing has been discontinued.

BRIEF STATEMENT OF THE INVENTION

This invention comprises a dental articulator of the Arcon type having a latch mechanism for releasably interlocking the upper and lower frame members in both the closed and open positions and, optionally, serving as a centric alignment mechanism. This latch mechanism can be employed on any Arcon type articulator having fully adjustable top, rear and medial fossa guides or can be used on Arcon type articulators having lesser adjustment capability. The latch mechanism comprises latch members which are located on respective ones of the upper and lower frames, typically at the center of lateral crossbars of these frame members which are coextensive with the condylar axis of the instrument. The latch members comprise a pin member which is supported along the condylar axis of the instrument by a pin mounting bracket and a cooperative hook arm member which is pivotally mounted on a second bracket member, the latter being slidably mounted on the lower frame member and being resiliently biased to locate the pivot axle of the hook arm member away from the pin member. The hook arm bears a detenting notch whereby this member is restrained in the pin detenting position and the frame members are interlocked with a slight compressive loading. The frame members are firmly seated in centric by detents carried on the superior fossa wall which seat their respective condyles in centric. Preferably, the hook arm has posteriorly projecting, resiliently biased lever arm that extends subjacent the lateral crossbar of the upper member so the opening of the articulator will depress the hook arm lever and engage the hook arm in its pin detenting position where it is restrained until a force is applied to the second bracket member, overcoming the force of the spring element resiliently biasing this member.

The invention also includes semi-adjustable capability of an articulator wherein the fossa guide elements that are carried by the upper frame member are provided with a varied selection of adjustment capability from simple slot guides in distal block members that are integrally formed with the laterial cross member to fossa guide members having a fixed rear wall at an average anatomical out and back incline and a lateral wall providing an immediate Bennett shift. The lateral wall can also bear interchangeable medial wall guides having fixed wall inclines. In another embodiment, means can be provided for independent adjustability of the angle of the eninentia and the angle of medial fossa guide as well as optional provision for an immediate side shift.

BRIEF DESCRIPTION OF THE DRAWINGS

The invention will be described with reference to the illustrations thereof which:

FIG. 1 is an elevational, partial cross sectional, side view of the instrument;

FIG. 2 is a rear elevational view of the instrument;

FIG. 3 is a partial sectional, elevational side view of the latch mechanism in its pin detenting position;

FIG. 4 is a view of an alternative incisal pin for the instrument;

FIG. 5 is a sectional view along lines 5—5 of FIG. 3;

FIG. 6 is a perspective view of the lower lateral cross member and associated latch member of the articulator;

FIG. 7 is a perspective view of the upper lateral frame member and its associated latch member; and FIGS. 8–10 illustrate the alternative upper lateral cross member having adjustable fossa guide elements.

DESCRIPTION OF THE PREFERRED EMBODIMENTS

Referring now to FIG. 1, the dental articulator is illustrated as an instrument having a lower frame member 10 and upper frame member 11. The instrument is of the Arcon type, having posterior condylar spherical elements 12 which are distally carried by a lower lateral cross member 14. The lower frame member has substantially vertical standards 16 at opposite sides thereof which extend into supporting engagement with the lateral cross member 14. The base 18 of the lower frame member extends anteriorly to an incisal pin support member 20 that is removably secured thereto by thumb screw 22. The base 18 of the lower frame member 10 also has a pair of posterior legs 24 and a pair of anterior legs 26, elevating base 18 above a work table or support, to provide vertical clearance to accommodate thumb screws 22 and 28, the latter extending through the base and having a threaded shank 30 for the removable attachment of dental cast support members, not illustrated. The base also bears one or more of pins 32 which, with shank 30 of thumb screw 28, index dental casts to the instrument.

The upper frame member 11 includes an upper lateral cross member 34 which, as the lower lateral cross member 14, extends coextensively with the condylar axis of the articulator. The condylar axis of the articulator extends through the centers of the spaced-apart, distally carried condylar sperical elements 12. The longitudinal member 36 of the upper frame member 11 extends anteriorly to support the incisal pin member, generally indicated at 38. This incisal pin member is carried at the anterior of the upper frame member 11 by thumb screw 40 which extends through a slot, not shown, in the leading edge of member 36 and into threaded engagement with a fore end bracket 42. Bracket 42 bears a flange 44 for abutment against the leading edge of member 36 and an integral, vertical bracket 46 having an arcuate face 48 which is engaged by a mating arcuate face of the head 50 of the incisal pin member 52. Head 50 has a vertical slot which receives the shank of thumb wheel 54, the latter extending through the slot and into threaded engagement with a bore in vertical bracket 46, whereby the vertical position of the incisal assembly can be fixedly adjusted on the anterior of the instrument, thereby providing for fixed adjustability of the spaced-apart positions of the upper and lower frame members in their closed position.

In the preferred embodiment, the incisal pin assembly can be provided with the fixedly adjustable shoe 56 having a key 57 that is slidably mounted in a groove of the mounting block 58 at the base of pin 52. The shoe 56 rests on an abutment surface, button 60, carried on the upper surface of the aforementioned incisal table 20.

The latch mechanism of the invention includes a pin member 62 centrally carried on the upper lateral cross member 34. This pin member, which is shown in greater detail in FIG. 7, comprises a bracket member 64 dependent from the undersurface of the upper lateral cross member and laterally, outwardly projecting pin shafts 66.

The other member of the hinge assembly of the invention comprises a latch hook arm generally indicated at 68 which is pivotally mounted on a pivot axle 70 which is secured to the lower lateral cross member 14 by bracket 72. The latter bracket is slidably mounted to the lower lateral cross member 14 by screw fasteners 74 which project through vertically elongated apertures 76 of bracket 72. Bracket 72 bears a posteriorly projecting flange 78 that extends beneath the lower lateral cross member 14. Preferably, the lower lateral cross member 14 has a central bore 80 that receives compression spring 82 which is biased betwen the flange 78 and the cross member 14 whereby bracket 72 is resiliently biased downwardly, away from the hinge pins 66.

The hook arm latch member 68 has a posteriorly directed arm 84 and a pin detenting notch 86 for resiliently restraining pin 66 when the hook arm member is rotated in the direction of arrow 88. Hook arm member 68 also bears a posteriorly projecting lever arm 90 which projects subjacent of the undersurface of the upper lateral cross member 34 so that rotational opening of the articulator by moving of the upper member along the arc shown by arrow 92 causes the posterior lower edge of the lateral cross member 34 to engage lever arm 90, deflecting this lever arm and pivoting the hook arm member 68 in the direction indicated by line 88, engaging the latch mechanism and interlocking the upper and lower frame members.

Referring now to FIG. 2, the articulator is illustrated in a rear elevational view. As there illustrated, upper frame member 34 bears distal fossa guide members 92 and 94 which have, on thier undersurface, slots 96 which are elongated in the anterior-posterior direction, i.e., longitudinal axis, of the instrument. Slots 96 receive the condylar, spherical elements 12 which are distally mounted on the lower lateral cross member 14. Elements 12 project on shafts 98 which are received within bores in the lower lateral cross member 14 and interlocked thereto by set screws 100. The lower frame member of the articulator has a base member 18 with posterior legs 24 and distal and upwardly projecting standards 16 that support opposite ends of the lower lateral cross member 14.

The view of FIG. 2 also shows that the flange 78 of bracket member 72 which projects beneath the center of lateral cross member 13 and is resiliently biased downwardly by compression spring 82. The upper end of bracket 72 is received between opposite side flanges 102 of the hook arm member 68 and bears the pivot axle 70 of the mounting of the hook arm member. The upper end of bracket 72 is grooved to receive a torsion spring 104 which has its opposite ends resiliently biased between the bracket 72 and the undersurface of the lever arm 90 whereby the hook arm member 68 is resiliently biased away from the pin member 62, assuming the position shown in FIGS. 1 and 2.

As previously mentioned, the hook arm member of the hinge assembly can be moved into a pin detenting position whereby the pin 66 is resiliently received within notch 86 of the hook arm member. FIG. 3 illustrates this view with the articulator in a closed position. The posteriorly projecting arms 84 of the hook arm member have been rotated past the point of engagement with pins 66 and for a sufficient distance that pins 66 are received within detenting notches 86 of the hook arm member. The hook arm member is restrained in this position, against the bias of torsion spring 104 by the downward force exerted by compression spring 82 which restrains the hook arm member and prevents its rotation to the unlocked position of FIGS. 1 and 2. The hook arm member can be released from its locking position by the application of a slight upward pressure on the undersurface of bracket 72, sufficient to overcome the resilient bias of compression spring 82 and permit upward translation of bracket 72 and hook arm member 68, whereby the posteriorly projecting arms 84 will clear pins 66, and permit rotation of the hook arm member to the open position shown in FIGS. 1 and 2.

The articulator as thus described can be supplied with alternate constructional features such as the alternate incisal pin member generally indicated at 110. This incisal pin member is similar in construction to the pin member 38 previously described in that it also has longitudinal rib 112 that is received in a slot in the leading edge of upper frame member 36, a flange 44 which serves as an abutment and forward stop for the frame member 36 and bracket 42 which has a threaded bore to receive the end of thumb wheel 40.

The vertical bracket 46 dependent from bracket 42 is shaped similarly to that previously described, with an arcuate forward face 48 that is in contact with a mating arcuate face of the head 50 of the incisal pin. The incisal pin 114 projects downwardly from the head 50 and bears a rounded lower end which is received in a concavity 116 of incisal table 118 which is carried on the lower frame member.

FIG. 5 illustrates the mounting means for the spherical condylar elements 12. As previously mentioned, these elements are carried at the upper end of shafts 98 which are received within bores 120 located at opposite ends of the lower lateral cross member 14. The shafts 98 are fixedly secured to lateral cross member 14 by set screws 100 which are engaged in threaded transverse bores 122 of the lower lateral cross member 13. Each shaft 98 bears a flat 124 for engagement by the set screw 100. Shaft 98 also has a rounded lower end 126 which projects into bore 120 to the position shown by broken line 128. In this position, the lower end of this shaft is engaged by the pointed, inboard end of set screw 130 whereby the advance of set screw 130 can provide a vertically adjustable abutment or stop for the shaft 98, and the spherical elements 12 can thereby be fixedly adjusted in a vertical direction by advance or retraction of set screw 130. Once the correct elevation is reached and the instrument thereby calibrated to an exact centric relationship of the upper and lower frame members, the shafts 98 are fixedly secured to the upper cross member 14 by set screws 100.

FIG. 6 is a perspective view of the lower lateral cross member 14 and associated structure as viewed from the rear of the instrument. As there illustrated, the lateral cross member 14 bears end portions 132 which are attached to the upper ends of standards 16 and locked thereto by screws 134 which engage threaded bores in standards 16. Screws 134 extend through bores 133 which are counterbored at 135 to receive the heads of the screws. Bores 133 are slightly oversized to permit horizontal alignment adjustment of the lateral cross member 14. The distally mounted spherically mounted condylar elements 12 are shown as supported by shafts 98. The flange 78 of bracket 72 projects beneath the undersurface of the lateral cross member 14. The hook arm member 68 of the hinge assembly is illustrated with its opposite side flanges 102 which receive, therebetween, the upper end of bracket 72. The bracket 72 is mounted in an upright, transverse groove 136 in the forward face of the lateral cross member 14.

The upper end of hook arm member 68 bears a pair of rearwardly projecting arms 84 with a central slot 138 to thereby define a clevis structure for receiving the pin bracket 64 of the pin member 62 of the latch assembly. Each of the opposite arms 68 bears a pin detenting notch 86, previously described.

Referring now to FIG. 7, the undersurface of the upper lateral cross member 34 is shown. As there illustrated, the forward edge of lateral cross member 34 is fixedly secured to the forwardly projecting frame member 36 by a groove (not shown) along the upper surface of the lateral cross frame member and by screws 140. The undersurface of lateral cross member 34 bears a central recess 142 in which is mounted the pin bracket 64 of the pin member 62. This bracket has a flat flange portion 144 which is bored to receive mounting screws 146 that secure the pin member 62 to the undersurface of lateral cross member 34. The bracket 64 bears laterally, outwardly projecting pins 66 which are engaged by the previously described hook arm member 68.

The lateral cross member 34 also distally carries opposite fossa guide blocks 150 which have the previously described, elongated slots 96 for receiving the spherical condylar elements 12.

As previously mentioned, the articulator also includes semi-adjustment capability whereby the instrument can be set to duplicate the most clinically significant mendibular movements. FIGS. 8–10 illustrate an embodiment of the invention having such capability. As there illustrated, the upper lateral cross member 35 bears distal clamp blocks 151 which have an arcuate surface and which have a central aperture 152 that is intersected by radial slot 154. Screw 155 (see FIG. 10) extends through slot 154 into a threaded bore whereby the block 151 can be compressed about shaft 156 to fixedly secure the latter. Aperture 152 receives trunion 156 that carries a semi-adjustable fossa guide assembly generally indicated at 158. The guide assembly 158 has an arcuate flange 160 which butts against the outer lateral face of block 151 and which bears indicia such as scale 162 (shown in FIG. 10) which cooperates with an index mark 163 on the posterior edge of block 151 whereby the angular orientation to the superior plate 164 of the guide assembly 158 can be observed.

The superior plate 164 has a posterior wall 166 which has a surface 168 with a curvilinear contour corresponding to average anatomical border movement of the mandibular for the rotating condular path. This rotating path is preset to an average anatomical inclination, out and back of approximately 25°, which is the angle of inclination of the surface area indicated at 170.

The undersurface of superior plate 164 preferably is grooved longitudinally at 183 to provide a guideway for an opposed condylar spherical element 12, useful in duplicating a protrusive mandibular movement. Groove 183 can be from 2 to about 5 millimeters in depth.

In the preferred embodiment, the medial wall bracket 180 is laterally adjustable on the fossa guide assembly 158. To this end, the forward face of the superior guide plate 164 bears groove 184 which receives rib 186 of the forward plate 188 of the medial wall bracket 180. The lateral position of the medial wall bracket 180 on the fossa guide assembly 158 is fixedly secured by a set screw 190 (see FIG. 9) which projects through a threaded bore in the top surface of superior guide plate 164 into groove 184, bearing against rib 186 and restraining the medial guide bracket 180. Indicia in the form of a scale 185 are provided on the top edge of medial guide bracket 180 to cooperate with an indicia in the form of scale 187 carried on superior plate 164 whereby the degree of lateral transaction of the medial wall bracket can be observed in a vernier manner and recorded.

The semi-adjustable fossa assembly 158 can also bear an adjustable, medial wall guide member. This guide member can be a small plate 172 pivotally carried on the undersurface of the lower edge 178 of medial wall bracket 180 by screw 174 which extends through arcuate slot 176 of plate 172. The lower edge 178 of bracket 180 can bear an arcuate groove 182 to provide for recessed mounting of the medial wall guide member.

The articulator as thus described has a number of significant features. The latch mechanism whereby the upper and lower frame members of the articulator can be interlocked in both the open and closed articulator positions constitutes a substantial advance in Arcon type articulators. This latch mechanism can be employed with substantially all Arcon type articulators since these commonly employ upper and lower lateral cross members that are coextensive with the condylar axis of the instrument. Because the upper and lower frame members of the articulators can be interlocked, the articulator can be inverted in an upside-down position for mounting of casts without use of a plastering stand.

The latch mechanism serves as an accurate locator of centric position of the frame members. The latch hook arm centers on the pin member, receiving the pin bracket member between its opposite arms. The downward force exerted on the upper frame member by the latch hook arm seats the condyles in their respective centric detents, thereby providing a centering action on the outboard fossa members that cooperates with the centering action of the latch hook arm and pin member.

The articulator having the limited or semi-adjustment capability is a useful tool for diagnosis and fabrication of restorations which can be made without the complexity of a pantograph and fully adjustable articulator. The semi-adjustment capability of the condylar fossa guide elements illustrated and described with regard to FIGS. 7-9 achieves duplication of the clinically significant movements of the mandible without encumbering the construction with less used, adjustment capabilities which characterize more recent advances in Arcon type articulators.

The invention has been described with reference to the illustrated and presently preferred embodiments thereof. It is not intended that the invention be unduly limited by this illustration and description of the presently preferred embodiment. Instead, it is intended that the invention be defined by the means, and their obvious equivalents, set forth in the following claims.

I claim:
1. A dental articular comprising:
   a lower frame member posteriorly bearing a pair of spaced-apart condylar elements with a condylar axis therebetween;
   an upper frame member pivotally carried thereon by spaced-apart fossa elements resting on said condylar elements;
   latching means including:
      pin means carried on one of said upper frame member coaxially to said condylar axis;
      hook arm means pivotally carried on said lower frame member whereby said hook arm means can be pivoted over said pin means to exert a downward force on said upper frame member; and
      detenting recesses on the undersurface of each of said fossa elements to seat their respective condylar elements.
2. The dental articulator of claim 1 including resilient latch means biased between said hook arm means and said lower frame member to resiliently bias said arm means from said pin means.

3. The articulator of claim 2 wherein said hook arm means bears detent notch means to receive said pin means whereby said latch resilient means restrains said hook arm means about said pin means when said hook arm means is pivoted into engagement with said pin means.

4. The articulator of claim 1 including a first bracket member slidably mounted on said other frame member and carrying said hook arm means.

5. The articulator of claim 4 wherein said first bracket member bears groove means to receive mounting screws that extend therethrough and engage threaded bores on said other member to provide said slidable mounting.

6. The articulator of claim 1 wherein said lower and upper frame members bear, respectively, lower and upper lateral cross members coextensive with said condylar axis.

7. The articulator of claim 6 wherein said condylar elements are a pair of spaced-apart spherical elements distally mounted on said lower lateral cross member and said upper frame member bears cooperative fossa guide members distally carried on the upper lateral cross member.

8. The articulator of claim 7 wherein said pin means include a support bracket carried on the undersurface of said upper lateral cross member and bearing distal pin means.

9. The articulator of claim 8 wherein said hook arm means has a central slot to receive said support bracket.

10. The articulator of claim 9 wherein said central slot of said hook arm means is tapered laterally outwardly at its leading edge.

11. The articulator of claim 1 wherein said hook arm means bears posteriorly projecting lever arm means.

12. The articulator of claim 11 wherein said lever arm means projects immediately subjacent of said upper, lateral cross member whereby pivotal movement of said upper frame member about said condylar axis engages said lever arm means and pivots said hook arm means into a detenting engagement with said pin means.

13. The articulator of claim 12 including second resilient means carried on said first bracket member and biasing said hook arm means away from said pin means.

14. The articulator of claim 1 wherein said cooperative fossa guide members comprise blocks integral with said upper, lateral cross member, each bearing a downwardly facing slot elongated in the longitudinal direction of said articulator.

15. The articulator of claim 1 wherein said fossa guide members are generally planar guide brackets pivotally carried on trunions secured by clamping block means of said upper lateral cross member.

16. The articulator of claim 15 wherein said fossa guide members bear medial wall guide means.

17. The articulator of claim 16 wherein said medial wall guide means are secured to said planar brackets by adjustment means permitting entirely lateral translation thereof.

18. The articulator of claim 17 wherein said planar guide brackets bear, on their undersurface, anterior-posterior detenting grooves for respective ones of said spherical elements.

19. The dental articulator of claim 1 wherein said fossa elements each include a medial wall bracket mounted thereon for fixedly adjustable lateral movement of said bracket and a medial wall guide pivotally mounted on said medial wall bracket.

20. The dental articulator of claim 1 wherein said fossa elements each include a medial wall bracket mounted thereon for fixedly adjustable lateral movement and a non-adjustable rear condylar guide wall having a rearwardly lateral incline of about 25°.

* * * * *